(12) United States Patent
Frodl

(10) Patent No.: US 7,805,256 B2
(45) Date of Patent: Sep. 28, 2010

(54) DYNAMIC MEASURED-VALUE FILTER FOR A GAS SENSOR ARRANGEMENT

(75) Inventor: Robert Frodl, München (DE)

(73) Assignee: Vincotech (Germany) GmbH, Unterhaching (DE)

( * ) Notice: Subject to any disclaimer, the term of this patent is extended or adjusted under 35 U.S.C. 154(b) by 383 days.

(21) Appl. No.: 11/737,010

(22) Filed: Apr. 18, 2007

(65) Prior Publication Data

US 2008/0114552 A1    May 15, 2008

(30) Foreign Application Priority Data

Apr. 27, 2006   (DE)   ........................ 10 2006 019 705

(51) Int. Cl.
*G06F 19/00* (2006.01)
*G06F 15/00* (2006.01)
(52) U.S. Cl. ........................... 702/24; 702/22; 702/23; 73/24.02; 73/24.03; 73/25.01; 250/565
(58) Field of Classification Search ............ 702/22–24; 73/25.01, 24.02, 24.03; 250/565
See application file for complete search history.

(56) References Cited

U.S. PATENT DOCUMENTS 6,843,102 B1 *   1/2005   Shulga et al.   ............... 73/25.01

* cited by examiner

*Primary Examiner*—Sujoy K Kundu
(74) *Attorney, Agent, or Firm*—Barley Snyder LLC

(57) ABSTRACT

A method of processing time-discrete measured values, which can be described in their time characteristic by a first exponential function which has a first time constant, the method comprising the steps of: detecting a first measured value and storing the first measured value, detecting a second measured value and storing the second measured value according to a defined time interval with respect to the detection of the first measured value, filtering the first measured value and second measured value by calculating a sum of the first measured value and a weighted difference between the second measured value and the first measured value, thereby generating time-discrete output values which can be described in their time characteristic by a second exponential function having a second time constant different from the first time constant, and outputting the output values is disclosed.

7 Claims, 6 Drawing Sheets

DYNAMIC MEASURED-VALUE FILTER FOR A GAS SENSOR ARRANGEMENT

CROSS-REFERENCE TO RELATED APPLICATIONS

This application claims the benefit of the filing date under 35 U.S.C. § 119(a)-(d) of document German Patent Application No. 10 2006 019 705.4; filed Apr. 27, 2006.

FIELD OF THE INVENTION

The present invention relates to a method for processing time-discrete measured values, which can be described in their time characteristic by means of an exponential function, the method making use of a measured-value filter. In particular, the present invention relates to a method of this kind for use in a gas sensor arrangement, and to a related gas sensor arrangement.

BACKGROUND

Known gas sensor arrangements comprise a radiation source emitting radiation, a gas measuring chamber, which can be filled with a sample gas that contains at least one analyte to be measured, and at least one detector device detecting radiation, which detector produces an output signal dependent on the presence and/or the concentration of the analyte. Gas sensor arrangements of this kind are known for the detection of a wide range of analytes, for example carbon dioxide or methane. Conventional gas sensors are based on the property of many polar gases to absorb radiation in the infrared (IR) wavelength range. The IR light is capable of causing excited states of the molecules by excitation of rotation and vibration oscillations by interacting with the dipole moment of the polar molecule. The thermal energy of the IR light is transferred to the gas in this way and in the same way the intensity of an IR ray passing through the gas volume is reduced. According to the excitation states, absorption occurs in a wavelength that is characteristic in each case of the gas in question, for example at 4.25 μm in the case of $CO_2$.

The detection of carbon dioxide ($CO_2$) in particular, is now becoming increasingly important in a large number of application areas. In the motor vehicle field, for example, carbon dioxide detection can be used to monitor the $CO_2$ content of the interior air to increase energy efficiency in the case of heating and air conditioning, in order to initiate a supply of fresh air via suitable fan flap activation only if required, i.e. when there is an increased $CO_2$ concentration. In addition, modern vehicle air conditioning systems are also based on $CO_2$ as a coolant, so that $CO_2$ gas sensors in the motor vehicle field can fulfill a monitoring function in connection with escaping $CO_2$ in the event of any defects. In the motor vehicle field in particular, gas sensors must meet the highest requirements in respect of sturdiness, reliability and miniaturizability. In addition, the response time of the sensor may not exceed certain limit values for safety applications.

The output signal of known detector devices, such as those disclosed in German patent application DE 10 2005 055 869.7, can be described quite generally as a response to an abrupt change in concentration by an exponential function according to the following equation (1).

$$y(t) = y_0 \cdot \left(1 - e^{\frac{-t}{\tau}}\right) \quad (1)$$

Here y(t) describes the detector signal emitted by the detector at a time t, $y_0$ the final value to which the detector signal approximates and τ the time constant of the exponential function.

To characterize the response behavior of the gas sensor, it is not the time constant τ, which describes the tangent to the exponential function at zero, which is used for the most part in practice, but the so-called $t_{90}$ time, which describes the time at which the detector signal has attained 90% of the final value $y_0$. Usually a $t_{90}$ time of less than 10 seconds is required for safety applications of a gas sensor.

However, various design boundary conditions that will be examined in greater detail below result in the $t_{90}$ time often being too long in the case of known gas sensors.

For example, the use of a filter membrane on the inlet opening, as is necessary to protect against pollution, causes a slower response of the gas sensor, in principle due to the retarded diffusion inwards. The stringent demands made on miniaturization of the gas sensor, furthermore, reduce the dimensions of the inlet opening for the sample gas and likewise lead to increased response times.

To increase the sensitivity of the sensor, it is proposed in German patent application DE 10 2005 055 860.7 to use a rotationally symmetrical cell. However, this implies an extended gas mixing time and thus once more an increase in the response time. Thus known gas sensors have the disadvantage that the $t_{90}$ time lays above the limit values required for safety applications.

On the other hand, the design conditions should be changed as little as possible, as otherwise, other disadvantages such as insufficient sensitivity have to be accepted.

SUMMARY

The present invention relates to a method of processing time-discrete measured values, which can be described in their time characteristic by a first exponential function which has a first time constant, the method comprising the steps of: detecting a first measured value and storing the first measured value, detecting a second measured value and storing the second measured value according to a defined time interval with respect to the detection of the first measured value, filtering the first measured value and second measured value by calculating a sum of the first measured value and a weighted difference between the second measured value and the first measured value, thereby generating time-discrete output values which can be described in their time characteristic by a second exponential function having a second time constant different from the first time constant, and outputting the output values.

BRIEF DESCRIPTION OF THE DRAWINGS

The invention is explained in greater detail below with reference to the accompanying Figures of which.

DETAILED DESCRIPTION OF THE EMBODIMENTS

The construction of the gas sensor arrangement according to the invention and the mode of operation of the method according to the invention for processing time-discrete measured values are to be explained in greater detail below with reference to the figures.

The present invention is based on the idea that an improved time characteristic of a gas sensor arrangement 100 as a whole can be achieved by the use of a filter stage in which the measured values of the detector unit 108 recorded at the time interval $\Delta t$ are converted into a time-discrete output function, which likewise obeys an exponential function but has a modified time constant. Due to the exponential step function response and the time-discrete mode of operation of the gas sensor 100, an additional differential portion can easily be introduced into the measuring signal, so that the sensor system as such has a faster time constant.

According to the invention, to calculate the output value, a sum of a first measured value and a weighted difference between a second measured value and the first measured value is calculated and the sum value used as the output value. This means that the output value is calculated as the sum of the previous measured value and the difference between the current measured value and the previous measured value multiplied by a weighting factor D. This relationship is described by the following equation (2):

$$z(t_i) = y_{i-1} + D \cdot (y_i - y_{i-1}) \quad (2)$$

Here $z(t_i)$ describes the value to be output currently in a time-discrete sequence of output values, $y_{i-1}$ describes the detector value at a first time, $y_i$ the detector value at a second time, which differs from the first time by the time interval $\Delta t$, and D the weighting factor.

The weighting factor D can be a fixed value with which a $\tau_2 \to 0$ can be set. Alternatively, the weighting factor D can also be a function, which is dependent on the difference $\Delta y$, i.e. the difference between the current measured value and the previous measured value. By using such an adjusted weighting factor, it is possible for example to set a new time constant $\tau_2$ and in addition, it is possible for example to prevent the noise from being increased excessively in the case of small changes.

Figure 1:
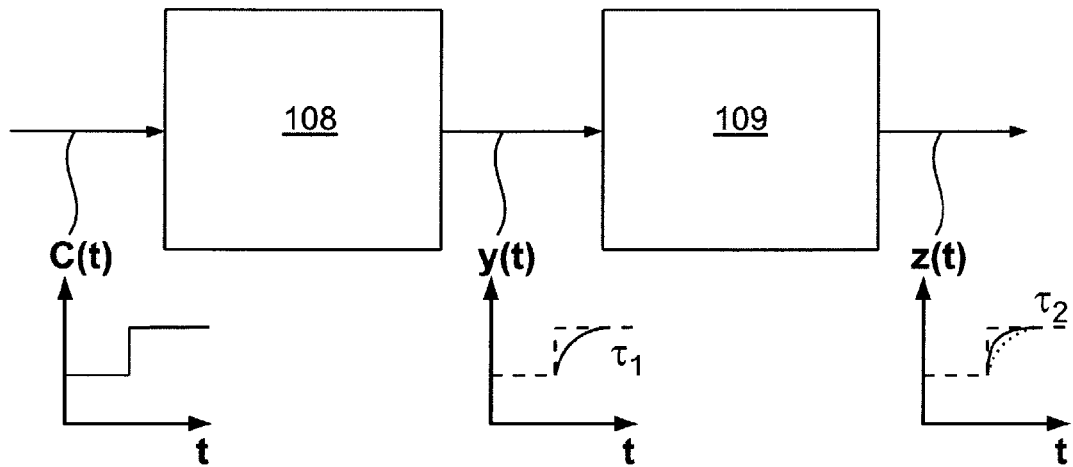
FIG. 1 shows a schematic representation of a detector unit with a filter according to the present invention.

As shown in FIG. 1, a detector unit 108 detects a gas concentration C(t), which can be assumed here approximately as a step function. It goes without saying, however, that the input signal for the detector unit 108 does not particularly have to be a gas concentration; rather the time characteristic of any sensor can be influenced according to the principles of the present invention.

The detector unit 108 supplies a time-discrete detector signal, which obeys a first exponential function y(t) and compared with the step function has a retarded response with a time constant $T_1$. By analogy with the general formulation of equation (1) the equation for the detector signal can be formulated according to the following equation (3):

$$y(t) = y_0 \cdot \left(1 - e^{\frac{-t}{\tau_1}}\right) \quad (3)$$

Here the detector signal according to the invention is defined in that it consists of time-discrete measured values $y(t_i)$, which are obtained at a time interval of $\Delta t$.

To be able to achieve a faster sensor characteristic, the detector signal is not used directly as the output signal according to the invention, but the detector signal is supplied to a filter unit 109, which carries out conversion of the detector signal y(t) to the output signal z(t). As indicated in FIG. 1, the output signal z(t) preferably has a shorter transient recovery time $\tau_2$.

The calculation rule for the conversion of the detector signal to the output signal is provided according to the invention by equation (2):

$$z(t_i) = y_{i-1} + D \cdot (y_i - y_{i-1}) \quad (2)$$

Figure 2:
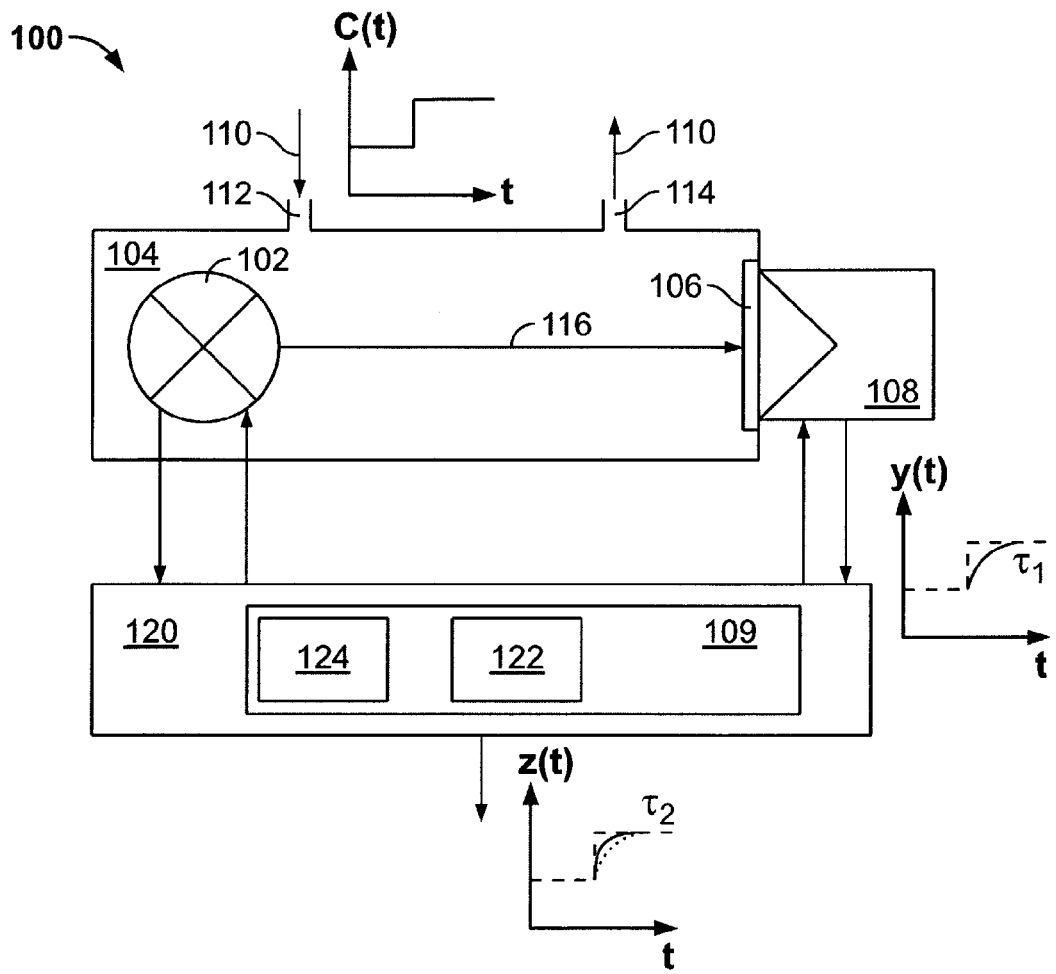
FIG. 2 shows a schematic representation of a gas sensor unit, which uses a filter method according to the present invention.

FIG. 2 shows an overview of a gas sensor arrangement that uses the filter unit according to the invention. As shown in this figure, the gas sensor arrangement 100 according to the invention comprises a radiation source 102, here a broadband infrared radiation source. In principle the gas sensor arrangement 100 shown is a so-called NDIR (non-dispersive infrared) sensor. Apart from the infrared radiation source 102, the basic components are the gas measuring chamber 104, a wavelength filter 106 and an infrared detector as the detector unit 108. The sample gas 110, which is to be checked for the gas component to be detected, is pumped into the gas measuring chamber 104 or diffuses into it, as symbolized by the inlet and outlet 112, 114. The presence and/or the concentration of the gas sought can, as explained above, be determined electrooptically via the absorption of a specific wavelength in the infrared range. As indicated in FIG. 2, the concentration of the gas sought can be approximated in the time range by a step function.

The infrared radiation 116 emitted is conducted through the gas measuring chamber 104 to the detector unit 108. Arranged on the detector unit 108 is an optical filter, which only allows through the wavelength range in which the gas molecules to be detected absorb. Other gas molecules do not normally absorb any light at this specific wavelength and therefore do not influence the amount of radiation reaching the detector unit 108 either. All suitable infrared detectors can be used as a detector unit and the method according to the invention can be adapted to any respective detector type.

For example, the detector can be a pyroelement, an infrared thermopile or a photodiode. The suitable detector in each case can be chosen according to the respective requirements. Thus the photodiode offers the advantage that it represents a comparatively low-cost component, while the thermocolumn, as the thermopile detector is also called, offers the advantage of particularly high and uniform absorption of the radiation in the selected spectral range. Finally, pyroelectric sensors have the advantage of a very high level of sensitivity and a miniaturized manufacturing capability.

According to the invention the infrared signal is pulsed by the radiation source 102, in order to be able to filter thermal background signals out of the desired signal. Thus the measured values supplied by the detector unit are present in the form of time-discrete values y(t), which, as indicated in FIG. 2, satisfy an exponential function with a first time constant $\tau_1$.

A controller 120 activates the radiation source 102 on the one hand and on the other receives the detector signals of the detector unit 108 and processes these further according to the principles of the present invention. In particular, the controller comprises a filter unit 109, which executes the conversion of the detector signal y(t) into an output signal z(t) with a shorter time constant $\tau_2$. As indicated schematically in FIG. 2, the filter unit 109 comprises a storage unit 122 for storing the measured values and a calculation unit 124, in which the conversion according to the filter function takes place. It goes without saying, however, that these two units can also be implemented in storage units and calculation units, for example microcontrollers, already used otherwise in the controller 120.

Figure 3:
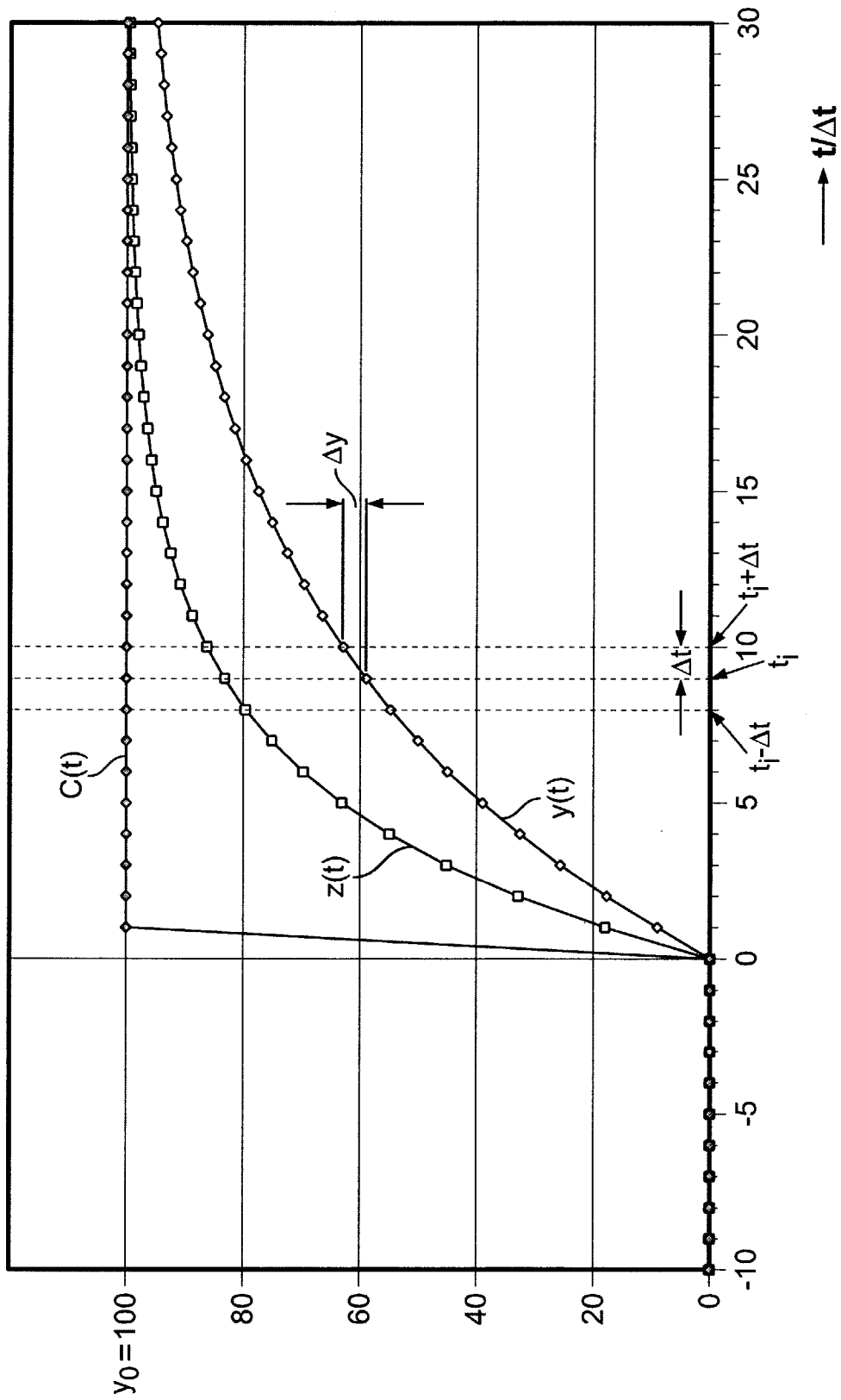
FIG. 3 shows a representation of the time characteristic of the detector signal, the output values and the change in concentration actually occurring as a function of time.

FIG. 3 shows in detail the time functions C(t), y(t) and z(t) represented statically in FIGS. 1 and 2. With reference to this graph the weighting factor D is to be deduced below in the equation (2).

First it should be noted that the present invention starts out from the basic condition that only a current value and the last value measured are available. As shown in FIG. 3, the individual measured values are each separated from another by a defined time interval $\Delta t$, for example 2.5 seconds. It is assumed for the following calculations that the gas concentration C(t) changes abruptly within a time interval $\Delta t$ from 0 to 100%. It should be taken into account here that the signal curves shown in FIG. 3 are standardized to $y_0$=100 for reasons of clarity. The curve y(t) obeys the equation (3) already mentioned, the time constant $\tau_1$, as already generally known, being correlated with the $t_{90}$ time by way of the following equation (4):

$$\tau_1 = -\frac{t_{90}}{\ln 0.1} \tag{4}$$

This means that to attain a shorter $t_{90}$ time according to the invention, the transient recovery time $\tau$ likewise has to be shortened. Such a function with reduced $\tau_2$ as output value function z(t) is represented schematically in FIG. 3. The function z(t) obeys the following equation (5):

$$z(t) = y_0 \cdot \left(1 - e^{\frac{-t}{\tau_2}}\right) \tag{5}$$

Since according to the invention the final value $y_0$ attained is to remain unchanged, it corresponds in equation (5) to the final value $y_0$ from equation (3). The fundamental exponential function characteristic is likewise supplied by the same function term as in equation (1). According to the invention only the $\tau_1$ achieved by the detector unit is replaced by the shorter $\tau_2$ of the equation (5). As is to be deduced in the following, the conversion from a current measured value y($t_i$) using the preceding measured value y($t_{i-1}$) to a current output value z($t_i$) is carried out via equation (2).

The following definitions are used for this: $t=t_{i-1}$ is a first time, at which a measurement is carried out; $t+\Delta t=t_i$ is a second time, which is $\Delta t$ later than $t_{i-1}$ and at which a second measurement is carried out. The difference between the measured values at the two times is described by $\Delta y$.

Using this nomenclature and the equations (3) and (5), the expression for the weighting factor D is to be deduced below.

For the first and second measured values measured at the respective first and second times, the following can be written:

$$y_1 = y_0 \cdot \left(1 - e^{\frac{-t}{\tau_1}}\right) \tag{6}$$

$$y_2 = y_0 \cdot \left(1 - e^{\frac{-(t+\Delta t)}{\tau_1}}\right) \tag{7}$$

From this it follows for the difference $\Delta y$ of the two measured values:

$$\Delta y = y_0 \cdot \left(e^{-\frac{t}{\tau_1}} - e^{\frac{-(t+\Delta t)}{\tau_1}}\right) \tag{8}$$

If equations (6) and (8) as well as the expression $$z_2 = y_0 \cdot \left(1 - e^{\frac{-(t+\Delta t)}{\tau_2}}\right) \tag{5'}$$

obtained from equation (5) are now inserted in equation (2), the following general expression for D results after corresponding resolution:

$$D = \frac{e^{-\frac{t}{\tau_1}} - e^{-\frac{(t+\Delta t)}{\tau_2}}}{e^{-\frac{t}{\tau_1}} - e^{-\frac{(t+\Delta t)}{\tau_1}}} \tag{9}$$

A substantial borderline case is the case in which $\tau_2$ is assumed to be 0, i.e. the case in which an ideal sensor, which exactly replicates the step function C(t), is achieved.

The limit value of the expression D for $\tau_2$ towards 0 is formed and the following simplified expression results for D, which is no longer dependent on time t:

$$\lim_{\tau_2 \to 0} D = \frac{1}{1 - e^{-\frac{\Delta t}{\tau_1}}} \tag{10}$$

If 9.8 seconds is inserted for $\tau_1$, for example, and 2.5 seconds for $\Delta t$, the weighting factor D assumes the value 4.17.

For any $\tau_2$ a further conversion is advisable, so that calculation of D is possible. First equation (6) is turned round so that the time t is expressed as a function of $y_0$ and $y_1$:

$$e^{-\frac{t}{\tau_1}} = 1 - \frac{y_1}{y_0} \tag{11}$$

and following logarithmising on both sides:

$$t = -\tau_1 \cdot \ln\left(1 - \frac{y_1}{y_0}\right) \tag{12}$$

If the equations (11) and (12) are put in equation (9) for the expressions $$e^{-\frac{t}{\tau_1}}$$

and t respectively, then the following general expression results for the weighting factor D:

$$D = \frac{1 - \frac{y_1}{y_0} - e^{-\frac{\tau_1}{\tau_2}\cdot\ln\left(1-\frac{y_1}{y_0}\right)}\cdot e^{-\frac{\Delta t}{\tau_2}}}{\left(1 - \frac{y_1}{y_0}\right)\cdot\left(1 - e^{-\frac{\Delta t}{\tau_1}}\right)} \quad (13)$$

The output value is thus multiplied by a weighting factor that is dependent in turn on the preceding measured value.

Figure 4:
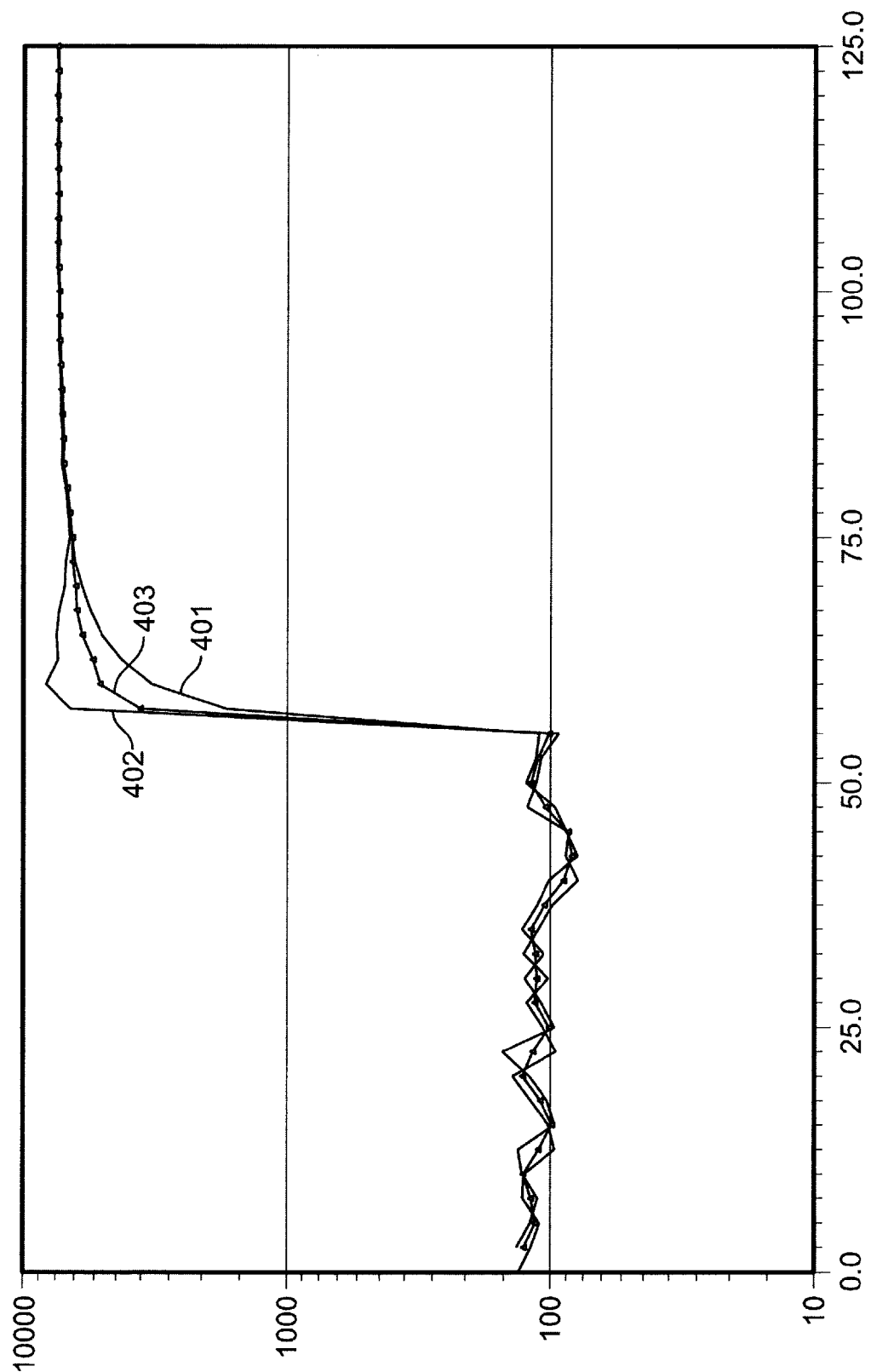
FIG. 4 shows a schematic representation of the time characteristic for various weighting factors D.
Figure 5:
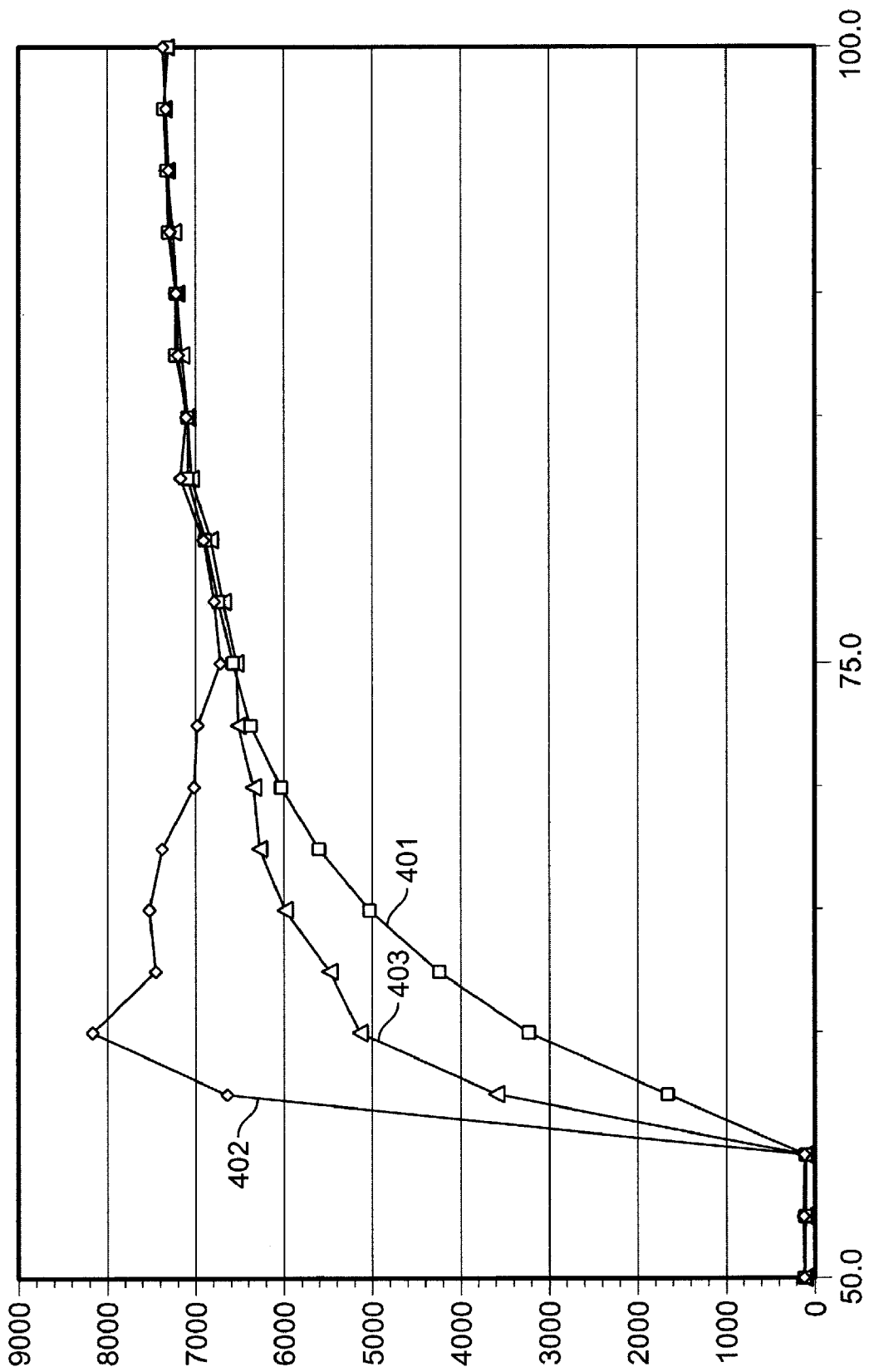
FIG. 5 shows a detail from FIG. 4 on a different scale.

FIGS. 4 and 5 show simulation results using two different values for the weighting factor D compared with the actual measured value curve 401 of the detector, FIG. 5 representing an enlarged detail from FIG. 4. Here curve 402 corresponds to a weighting factor D=4.17, which corresponds approximately to the limit value for $\tau_2 \to 0$, so that curve 402 has a substantially shorter time constant than the detector signal 401. The simulation results show a slight overshoot for this case, though, so that an adjustment using smaller D values seems sensible. Curve 403 represents the output values for such a weighting factor D=2.23.

A further basic condition when operating a gas sensor in a motor vehicle application is the safety requirement that a rising edge with the change in concentration of 1,000 ppm per second must be at least still detectable. On the other hand, the conversion to the accelerated output signal should not take place if possible in the event of very small differences between the first and the second measured value Δy, in order to prevent noise that is too strong.

Figure 6:
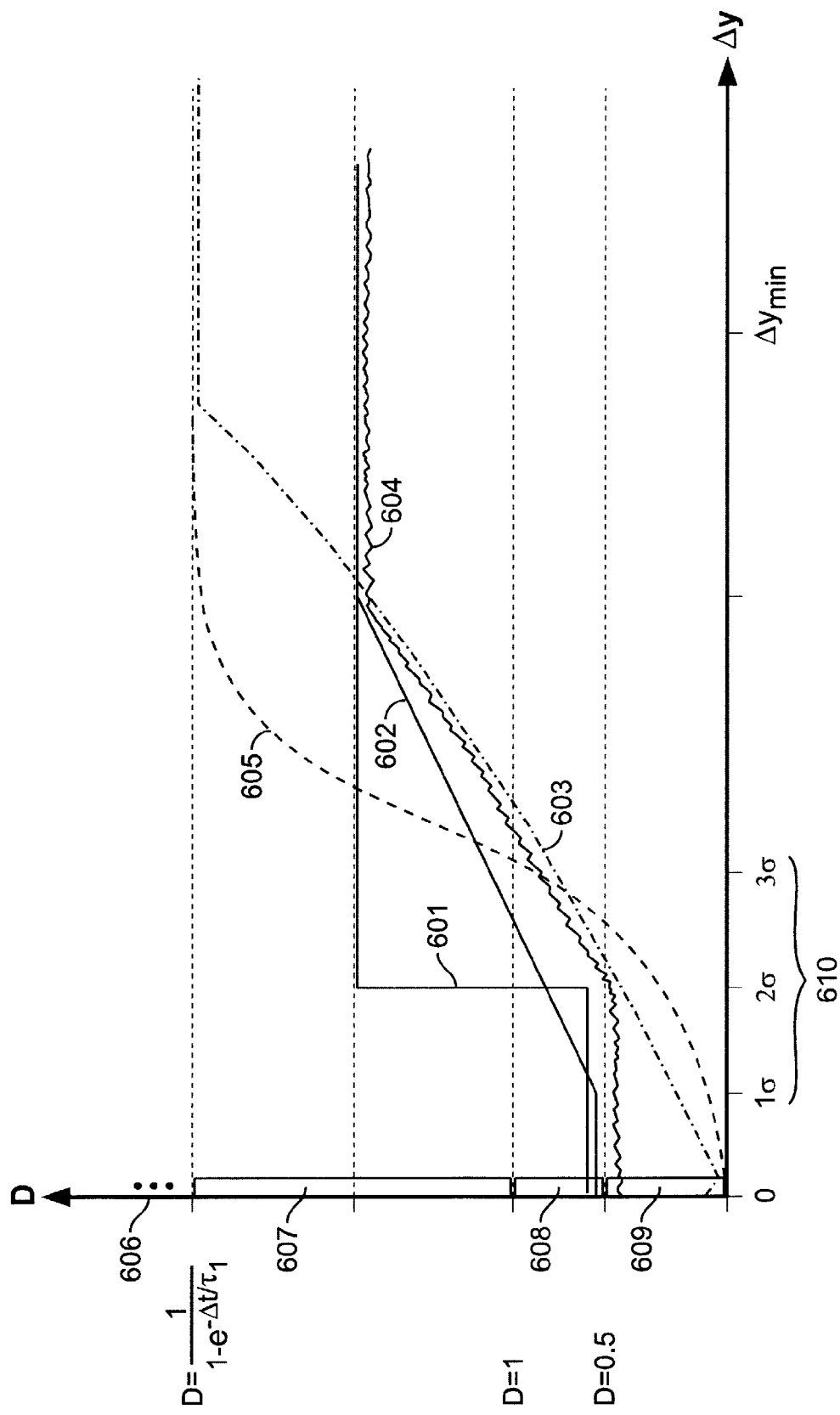
FIG. 6 shows various weighting factors depending on the difference between two detector signals.

It can be shown that, depending on the absolute value for Δy, various weighting factors D can make sense. These relationships are shown in FIG. 6. For values below a defined $\Delta y_{min}$ lower D values are expediently chosen to configure the sensor to be more sluggish and so avoid excessive noise and overshooting.

Above the defined value $\Delta y_{min}$, the aim is for the response time to be fast, and so above this minimum value filtering takes place using higher D values. The minimum Δy value, up to which the sensor should tend to be sluggish, can be calculated approximately using the following equation (14).

$$\Delta y_{min} = y_s \cdot \left(1 - e^{-\frac{\Delta t}{\tau_1}}\right) \quad (14)$$

In the case that an edge of 1,000 ppm per second should be reached and the interval between two measurements is 2.5 seconds, $y_s$=2,500 ppm and at $\tau_1$=22.5 s a value $\Delta y_{min}$ of 564 ppm results. If the real time constant value $\tau_1$ is still lower, for example 40 seconds, $\Delta y_{min}$ falls to 335 ppm.

As shown in FIG. 6, the D value that leads to an accelerated system response must be attained at the latest according to the invention for $\Delta y = \Delta y_{min}$. This can be achieved here, as shown for example as curve 601, by a simple step function, but also more complex dependencies $D(\Delta y_{min})$ can be chosen, which are to be explained below with reference to the curves 602 to 605.

The step function 601 uses a constant value of D=0.5 until Δy is distinguished from the noise 610 (here the value 2σ is chosen by way of example). Filtering using D=0.5 corresponds to simple averaging. For $\Delta y > \Delta y_{min}$ a value between D=1 and $$D = \frac{1}{1 - e^{-\frac{\Delta t}{\tau_1}}}$$

is entered for D, so that the output values have a reduced time constant $\tau_2$. Curve 602 outlines the case in which the new D value is approximated already after 1σ slowly in the form of a linearly rising dependence on Δy.

Such a linear dependence could also, as curve 603 outlines, begin at Δy=0 and rise as far as a value of $$D = \frac{1}{1 - e^{-\frac{\Delta t}{\tau_1}}},$$

which must be attained at the latest for $\Delta y = \Delta y_{min}$. In principle any dependencies can be realised in the calculation unit 124 of the filter 109 according to the invention, as indicated by the curved progression of curve 605.

For D values $$D > \frac{1}{1 - e^{-\frac{\Delta t}{\tau_1}}}$$

(characterized by the area 606 in FIG. 6) the system shows a strong overshoot, while in the area 607, i.e. for $$1 < D < \frac{1}{1 - e^{-\frac{\Delta t}{\tau_1}}},$$

the contraction according to the invention in the transient recovery time is attained. In the area 608, i.e. for D values between 1 and 0.5, the system is more sluggish than the transient recovery time of the detector actually prescribes, and for values below D=0.5 (area 609) the sensor "hangs" on the respectively preceding measured value as shown by curve 604.

Using the measured value filtering according to the invention, especially in connection with gas sensors, a faster response of the entire sensor system to abruptly increased gas concentration values can be achieved. Although above it was the special case of an NDIR-$CO_2$ sensor that was being described throughout, it is clear that the present invention can be adapted to all sensor systems in which an exponential approximation to a final value takes place and in which the measured values are present in time-discrete form.

Furthermore, the calculations executed above are based exclusively on the assumption that the measuring signal, starting out from the initial value 0, approaches the final value $y_0$ in a positively rising manner. It can be shown, however, that the principles according to the invention can be transferred by analogy also to the case of an exponential decay according to the general equation $$y(t) = (b - a) \cdot e^{-\frac{t}{\tau_1}} + a \quad (15)$$

in which case b describes the start value of the decaying signal and the final value to which the signal for $t \to \infty$ approximates.

Finally, a gas sensor arrangement with only one radiation source and only one detector was always assumed above.

Figure 7:
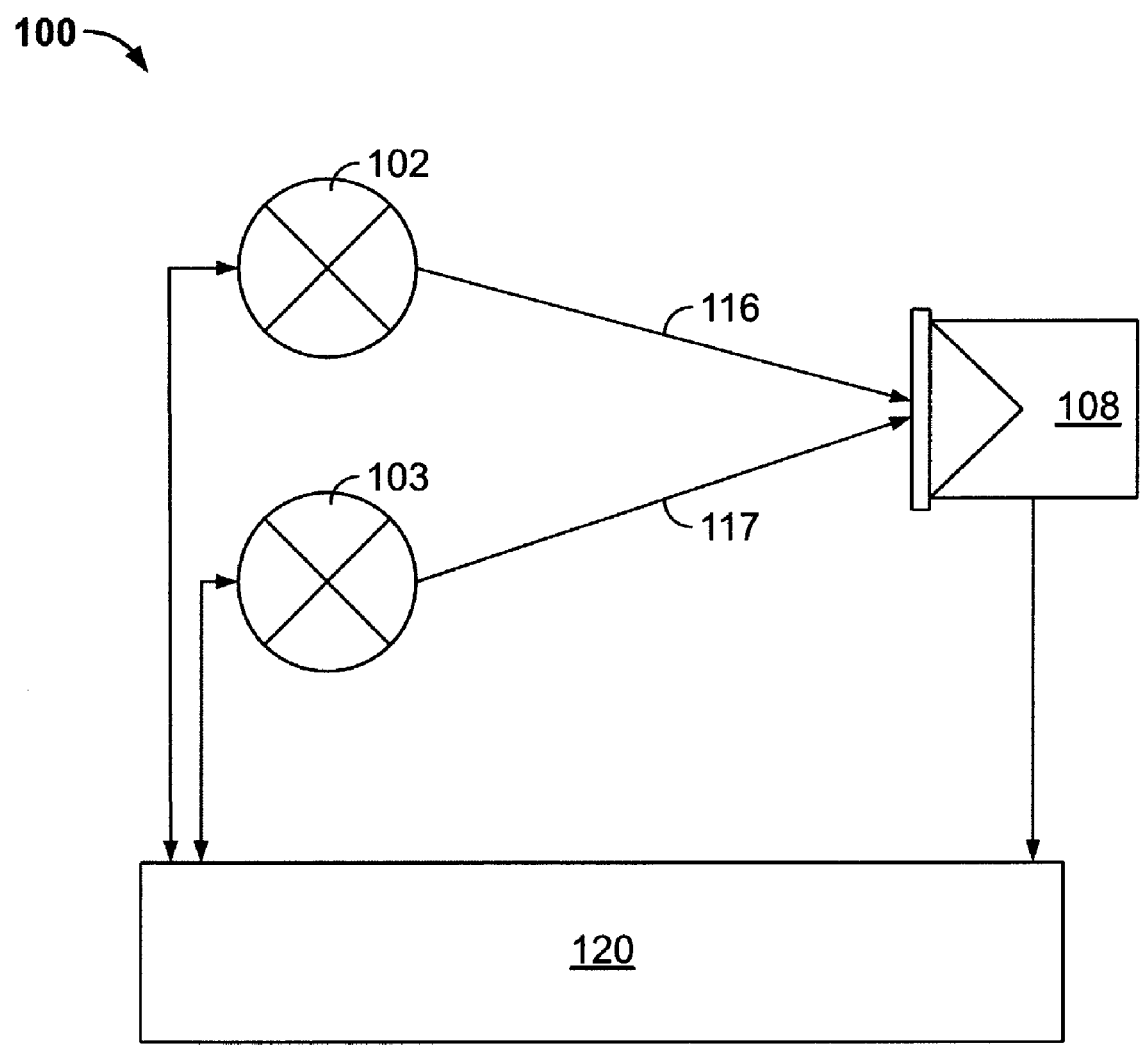
FIG. 7 shows schematic representation of an alternative embodiment of a gas sensor arrangement with two radiation sources according to the present invention.

Naturally, all known referencing principles, such as of two radiation sources or of more than one detector, for example, can also be used. For example, FIG. 7 shows such an arrangement schematically with two radiation sources, which can be used to eliminate signs of ageing in the infrared radiation source.

The above described solutions according to the present invention provide the advantage that a faster response of the sensor 100 to an abrupt increase in the gas concentration can be guaranteed without having to resort to design measures.

The advantageous properties of the measured-value processing according to the present invention can be exploited, in particular, in gas sensor arrangements for the detection of carbon dioxide, for example in the motor vehicle field, both for monitoring $CO_2$ escaping from leaks and for verifying the air quality in the passenger interior. Naturally, the principles according to the invention can also be used in connection with the detection of any other gases and are of significance for all sensors in which a measuring signal obeys an exponential function with a first time constant and output values are to be obtained that obey an exponential function with a changed time constant.

The foregoing illustrates only some of the possibilities for practicing the invention. Many other embodiments are possible within the scope and spirit of the invention. It is, therefore, intended that the foregoing description be regarded as illustrative rather than limiting, and that the scope of the invention is given by the appended claims together with their full range of equivalents.

What is claimed is:

1. A method of processing time-discrete measured values, which can be described in their time characteristic by a first exponential function which has a first time constant, the method comprising the steps of:
    detecting a first measured value and storing the first measured value;
    detecting a second measured value and storing the second measured value according to a defined time interval with respect to the detection of the first measured value;
    filtering the first measured value and second measured value by calculating a sum of the first measured value and a weighted difference between the second measured value and the first measured value through a controller, thereby generating time-discrete output values which can be described in their time characteristic by a second exponential function having a second time constant different from the first time constant; and
    outputting the output values.

2. The method according to claim 1, wherein the weighted difference is calculated by multiplying the difference by a constant factor.

3. The method according to claim 1, wherein the weighted difference is calculated by multiplying the difference by an adjustable factor.

4. The method according to claim 3, wherein the adjustable factor is dependent upon a value of the difference between the second measured value and the first measured value.

5. A method of operating a gas sensor arrangement having a radiation source, a measuring chamber, a detector device configured to produce a detector signal ($y(t)$), and a control unit for recording the detector signal ($y(t)$) and outputting an output signal ($z(t)$), the method comprising the steps of:
    detecting a first measured value of a gas concentration and storing the first measured value;
    detecting a second measured value of the gas concentration and storing the second measured value according to a defined time interval with respect to the detection of the first measured value;
    filtering the first measured value and second measured value by calculating a sum of the first measured value and a weighted difference between the second measured value and the first measured value, thereby generating time-discrete output values which can be described in their time characteristic by a second exponential function having a second time constant different from the first time constant; and
    outputting the output values as output signal ($z(t)$).

6. The method according to claim 5, wherein the gas concentration is a concentration of a gaseous analyte.

7. The method according to claim 5, wherein the gas concentration is a concentration of carbon dioxide.

* * * * *